(12) United States Patent
Sim et al.

(10) Patent No.: US 7,749,519 B2
(45) Date of Patent: Jul. 6, 2010

(54) UNIQUE DNA AND POLYPEPTIDE SEQUENCES BASED ON THE CIRCUMSPOROZOITE PROTEIN OF PLASMODIUM VIVAX

(76) Inventors: Kim Lee Sim, 12115 Parklawn Dr., Rockville, MD (US) 20852; Stephen Hoffman, 12115 Parklawn Dr., Rockville, MD (US) 20852; Myriam Arevalo, Instituto de Inmunologia Call4B Edificio de Microbilogia, 3er Plso, Universidad del Valle, Sede San Frernando, AA 25574, Centro Internacional de Vacunas, Carrera 35 #4A-53, A.A. 26020, Cali (CO); Socrates Herrera, Instituolo de Inmunologia, Calle 4B #38-00, Edificio de Microbiologia, 3er Plso, Universidad del Valle, Soda San Fernando, AA 25574, Centro Internacional de Vacunas. Carrera 35 #4A-53. A.A. 26020, Cali (CO)

( * ) Notice: Subject to any disclaimer, the term of this patent is extended or adjusted under 35 U.S.C. 154(b) by 115 days.

(21) Appl. No.: 11/637,567

(22) Filed: Dec. 11, 2006

(65) Prior Publication Data

US 2008/0057085 A1    Mar. 6, 2008

Related U.S. Application Data

(60) Provisional application No. 60/748,779, filed on Dec. 9, 2005.

(51) Int. Cl.
*A61K 39/00* (2006.01)
*A61K 39/38* (2006.01)
*A01N 43/04* (2006.01)
*C07H 21/02* (2006.01)
*C07H 21/04* (2006.01)

(52) U.S. Cl. .................. 424/269.1; 424/184.1; 514/44; 536/23.1; 536/23.7

(58) Field of Classification Search ........................ None
See application file for complete search history.

(56) References Cited

FOREIGN PATENT DOCUMENTS

WO    WO 87/00533    * 1/1987
WO    WO 01/55181 A2 * 8/2001

OTHER PUBLICATIONS

Struik and Riley, Immunological Reivews 2004, vol. 201:268-290.*
Oplinger et al NIH record vol. LVII No. 9, 2005.*
Tongren et al. Trends in Parasitology vol. 20 Dec. 2004 p. 604-610.*
Rogers et al, Vaccine 17:3136-3144, 1999.*
Ellis, R.W. (Chapter 29 of "Vaccines" [Plotkin, S.A. et al. (eds) published by W. B. Saunders company (Philadelphia) in 1988.*
Abbas et al. Cellular and Molecular Immunology 2000 Chapter 15 p. 360-362).*
Definition of Vaccine: The Dictionary of Immunology, Herbert et al eds, Academic Press, 1995.*
Greenspan et al, Nature Biotechnology 17:936-937, 1999.*
Colman et al. (Research in Immunology 145: 33-36, 1994.*
Harlow et al , Antibodies A Laboratory Manual, Cold Spring Harbor Laboratory Press Inc., 1988, see pp. 23-25, 27-33 and 72-74.*
Houghten et al. New Approaches to Immunization, Vaccines 86, Cold Spring Harbor Laboratory, p. 21-25, 1986.*
Molling et al. J Mol. Med (1997) 75: 242-246.*
Tighe et al. Immunology Today vol. 19, p. 89-97.*
Dittmer et al Current Opinion in Microbiology vol. 6 Oct. 2003 p. 472-477.*
Charoenvit et al. Science vol. 251, No. 4994, Feb. 8, 1991, pp. 668-671.*

* cited by examiner

*Primary Examiner*—Robert Mondesi
*Assistant Examiner*—Oluwatosin Ogunbiyi
(74) *Attorney, Agent, or Firm*—David Dolberg, Esq.

(57) ABSTRACT

Malaria in humans is caused by infection with *Plasmodium* species parasites including *P. vivax*. The biology and immunobilogy of *P. vivax* is distinct from that of *P. falciparum*. Provided are unique synthetic polypeptides and DNA molecules which encode them. Each of these molecules correspond to regions of the circumsporozoite protein of *P. vivax*. Each molecule comprises sequences corresponding to several repeats of the central region of the Pv 210 variant fused to sequences corresponding to several repeats of the central region of the Pv 247 variant. Each molecule additionally comprises sequences corresponding to either the amino terminus, the carboxy terminus, or both the amino and carboxy termini of the PvCSP. Also provided are vaccines comprising these unique sequences and methods of using these vaccines and sequences to prevent and treat Pv malaria.

7 Claims, 7 Drawing Sheets

Schematic of codon optimized genes

Protein 1: Nt — | N-terminal | RcRv | — Ct

Protein 2: Nt — | RcRv | C-terminal | — Ct

Protein 3: Nt — | N-terminal | RcRv | C-terminal | — Ct

- N-terminal domain is composed of the amino region
- RcRv domain is composed of multiple units of the common repeat (VK210) and multiple units of the variant repeat (VK247)
- C-terminal domain is composed of the carboxyl region 30 ul/lane supernatant from culture broth collected at time points post methanol induction, reducing conditions. Supernatants are from shake flask fermentations.

Antibody titers in mice immunized with *Pv*CSP Protein 1 or adjuvant alone and assessed for antibodies to *Pv*CSP Protein 1 by ELISA. The data represent the serum dilution at which the optical density was 1.0 (OD 1.0) for individual mice. In mice immunized with *Pv*CSP Protein 1 the mean serum dilution at which the optical density was 1.0 was 57,423. In control mice the OD 1.0 was 77.

Antibody titers in mice immunized with *Pv*CSP Protein 3 or adjuvant alone and assessed for antibodies to *Pv*CSP Protein 3 by ELISA. The data represent the serum dilution at which the optical density was 1.0 for individual mice (OD 1.0). In mice immunized with *Pv*CSP Protein 3 the mean serum dilution at which the optical density was 1.0 was 72,520. In control mice the OD 1.0 was 492.

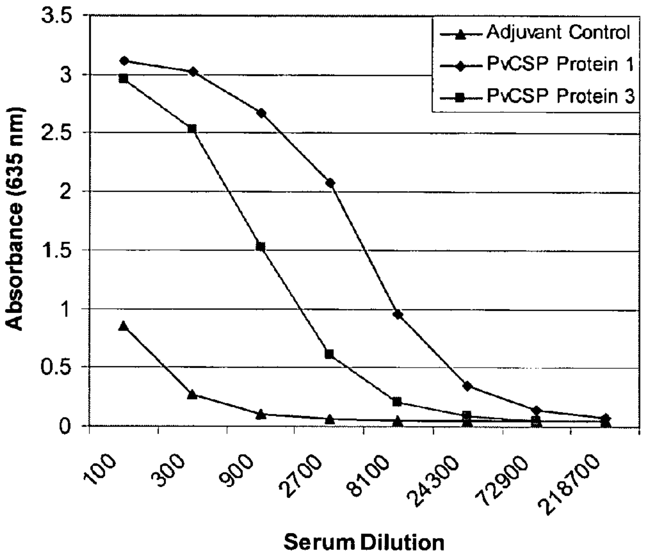

Antibodies to the *Pv*CSP 210 repeat region peptide (common) in sera of mice immunized with *Pv*CSP Protein 1, *Pv*CSP Protein 3, or adjuvant. Sera from all mice (n = 10) in each group were pooled and assessed by ELISA using a synthetic peptide containing repeat 210 (common repeat) as coating antigen. Mice immunized with each of the proteins produced antibodies to this repeat region peptide sequence.

FIGURE 5

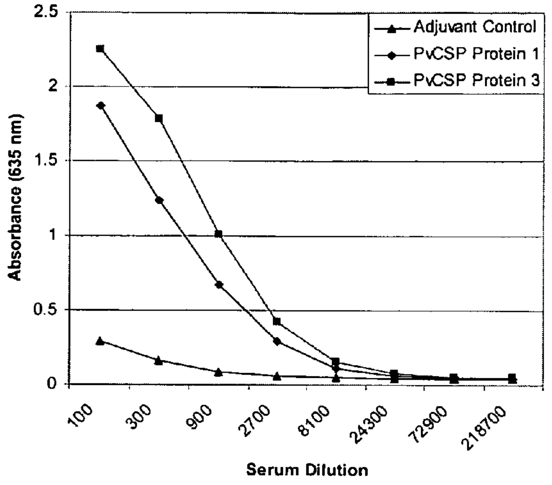

Antibodies to the *Pv*CSP 247 repeat region peptide (variant) in sera of mice immunized with *Pv*CSP Protein 1, *Pv*CSP Protein 3, or adjuvant. Sera from all mice (N=10) were pooled and assessed by ELISA using a synthetic peptide containing repeat 210 (variant repeat) as plate antigen. Mice immunized with each of the proteins produced antibodies to this repeat region peptide sequence.

FIGURE 6

Interferon gamma ELIspot results in mice immunized with *Pv*CSP Protein 1 in adjuvant, *Pv*CSP Protein 3 in adjuvant, or adjuvant alone (control).

UNIQUE DNA AND POLYPEPTIDE SEQUENCES BASED ON THE CIRCUMSPOROZOITE PROTEIN OF *PLASMODIUM VIVAX*

CROSS-REFERENCE TO RELATED PATENT APPLICATIONS

This application claims priority from U.S. Provisional Application 60/748,779 filed 09 Dec. 2005, incorporated herein by reference in its entirety.

FIELD OF THE INVENTION

This invention relates generally to unique DNA sequences, unique polypeptides, recombinant and synthetic DNA and encoded polypeptides based upon the natural sequences of the malaria-causing parasite *Plasmodium vivax* (hereinafter "Pv"). More particularly, the invention relates generally to unique DNA and encoded polypeptides that are based upon the circumsporozoite protein of Pv (hereinafter, "PvCSP"), as well as vaccines which utilize these compositions.

BACKGROUND

1) Impact of Malaria: Malaria affects 300-500 million and kills 1-3 million individuals annually, and has an enormous economic impact, especially in sub Saharan Africa. Cumulative Gross Domestic Product of malaria endemic countries may have been reduced by 50% over the past 20 years compared with non malarious countries, and malaria was responsible for much of that loss. The World Tourist Organization reported that in 2000 there were 17.1 million international travelers to sub-Saharan Africa, 19.8 million to Central and S. America, and 46.6 million to SE Asia. It is estimated that more than 10,000 travelers from N. America, Europe, and Japan contract malaria/year. For more than 100 years during every military campaign conducted where malaria was transmitted, U.S. forces have had more casualties from malaria than from hostile fire; an estimated 12,000,000 person days lost during WW II and 1.2 million during the Vietnam conflict; at least half of these casualties were due to Pv. More than 40% of the world's population is at risk of *P. vivax* and there are an estimated 147 to 436 million new clinical cases annually of *P. vivax* malaria in the world. This is a dramatic increase over previous estimates (Mendis, K., et al., *The neglected burden of Plasmodium vivax malaria*. Am J. Trop Med Hyg, 2001. 64(1-2 Suppl): p. 97-106). The incidence and range of endemic malaria caused by Pv has expanded during the past 30 years and resistance to standard therapy could be widespread. Pv disease is further complicated by hypnozoites, the parasite form in the liver, creating a persistent reservoir of infection.

2) Immunity to malaria: Individuals repeatedly exposed to malaria in endemic areas develop a high degree of clinical immunity by the age of 10-15 yrs that protects them from the clinical manifestations of infection (Gunewardena, D. M., R. Carter, and K. N. Mendis, *Patterns of acquired anti-malarial immunity in Sri Lanka*. Mem Inst Oswaldo Cruz, 1994. 89(Suppl 2): p. 63-5.) Additionally, transfer of antibodies and cells from immune individuals and animals to susceptible hosts induces protection against malaria infections, and immunization of humans with both *Plasmodium falciparum* (Pf) and Pv irradiated parasites has led to sterile immunity. However, Pv has its own distinct biological properties and there is little evidence for cross-protective immunity between these *Plasmodium* species (Id.). In contrast, extensive data from the study of human malarial infections induced under controlled conditions indicate that immunity to each species is acquired in a species-specific manner (Collins, W. E. and G. M. Jeffery, *A retrospective examination of sporozoite- and trophozoite-induced infections with Plasmodium falciparum in patients previously infected with heterologous species of Plasmodium: effect on development of parasitologic and clinical immunity*. Am J Trop Med Hyg, 1999. 61(1 Suppl): p. 36-43.). It is therefore unlikely that Pv would be controlled by vaccines that may eventually be developed against Pf, indicating that Pv control will require a Pv specific vaccine. Since both parasite species coexist in most endemic areas of the world and little reduction will be observed on the overall malaria burden if a Pf vaccine alone was applied, inclusion of vaccine subunits targeting each species would be desirable in any vaccine for mass application.

3) Status of malaria vaccine development: Three approaches have been used to develop malaria subunit vaccines. The first is to create vaccines that target sporozoites as they enter the body and invade and reproduce in the liver (pre-erythrocytic stage vaccines). These have the potential to limit or prevent infection altogether. The second is to limit parasite invasion of erythrocytes and subsequent multiplication and pathological effects (asexual erythrocytic stage vaccines). Such vaccines would only limit severe disease—they would not prevent infection or mild disease. The third strategy is to prevent the spread of viable parasites to other people with transmission-blocking vaccines. These stimulate the production of antibodies that are ingested when the parasite is sucked up by a new mosquito. The antibodies destroy the parasite within the vector's gut. All 3 strategies of vaccine design are now being pursued, thanks to recent increases in funding. Current vaccine candidates in clinical trials, however, contain just one or a few proteins. According to the World Health Organization (www.who.int/vaccine research/documents/en/malaria table.pdf), there are currently more than 70 malaria vaccine candidates being studied, but only a few are at the Phase 2b (assessment of protection in the developing world). Very few III of the vaccine on the list are for *P. vivax*, and no *P. vivax* vaccine is beyond Phase I clinical trials.

a. Only one malaria protein, the *P. falciparum* circumsporozoite protein (PfCSP) has been repeatedly evaluated in clinical trials and shown to provide complete protection in a portion of volunteers. No other candidate protein has been shown to reproducibly protect humans in such studies. The lead candidate based on the PfCSP is called RTS,S/AS02A. In its first trial, the vaccine protected 6 out of 7 volunteers against *P. falciparum* challenge 3 weeks after the last immunization, and in subsequent tests it protected 40-50% of volunteers within 2-3 weeks of immunization Kester, K. E., McKinney, D. A., Tornieporth, N. et al. (*Efficacy of recombinant circumsporozoite protein vaccine regimens against experimental Plasmodium falciparum malaria*. J Infect Dis, 2001. 183: p. 640-647).

4) Pv Pre-erythrocytic Vaccines: The aim of a pre-erythrocytic vaccine is to prevent entry of sporozoites into hepatocytes and further development into tissue schizonts. This blocks the clinical manifestations of disease and further transmission of the parasites to the mosquito. Immunization of malaria-naive volunteers by bite of mosquitoes infected with Pf previously exposed to irradiation (15-20 kRad) consistently protects them against challenge with infectious sporozoites (Hoffman, S.L. and D.L. Doolan. *Malaria vaccines-targeting infected hepatocytes*. Nat Med,2000. 6(11): p. 1218-9). Protection depends on responses that arrest parasite development in the liver by direct cytolysis of infected hepatocytes, through the release of cytokines like IFNI gamma (Donlan. D.L. and S.L. Hoffman.*The complexity of protective immunity against liver-stage malaria*. J Immunol, 2000. 165 (3): p. 1453-62) or IL-6 (Pied. S., at al., *IL-6 induced by IL-1 inhibits malaria pre-erythrocytic stages but its secretion is down-regulated by the parasite*. Journal of immunology. 1992. 148(1): p. 197-201). Or through the of INOS synthase (Seguin. M.C.. et al.. *induction of nitric oxide synthase protects against malaria in mice exposed to irradiated Plasmodium berahei infected mosquitoes: involvement of interferon gamma and CD8+T* cells. J Exp Med. 1994.130(1): p. 353-8). Sera and cells from individuals immunized with irradiated soorozoites have allowed the identification of multiple Pfore-erythrocytic antigens and indirectly Pv proteins. PvCSP and PvSSP2. Antibodies recognize the CSP and induce a 143 precipitation reaction on the surface of live sporozoites that neutralizes sporozoite invasion into hepatocytes. The genes encoding the PfCSP and PvCSP (Arnot. D.E.. et al.. *Circumsporozoite protein of Plasmodium vivax: gene cloning and characterization of the immunodominant epitope*. Science. 1985. 230(4727): p. 815-8) have been cloned and sequenced. The PvCSP from the strain of Pv that was sequenced is composed of 373 amino acids and shows high similarity to those corresponding to other Plasmodia species (Sinnis. P. and V. Nussenzweig. *Preventing sporozoite invasion of hepatocytes. in Malaria vaccine development. A multi*151*-immune response approach*, S.L. Hoffman. Editor. 1996. ASM Press: Washington. D.C. p. 15-34). it is characterized by a central domain flanked by short repetitive units flanked by non-repetitive amino (N) and carboxyl (C) fragments. The flanking regions contain small stretches of highly conserved sequences designated Region I and Region II-plus that appear to represent ligand domains for invasion to the hepatocyte (Cerami, C., et al., *The basolateral domain of the hepatocyte plasma membrane bears receptors for the circumsporozoite protein of Plasmodium falciparum spz*. Cell, 1992. 70(6): p. 1021-33). The central PvCSP domain is composed of 19 blocks of 9 amino-acids each. There are two allelic forms present in nature, the VK210 (Pv210) or common type (GDRADGQPA) (SEQ ID NO: 11). which is present in the first PvCSP gene sequenced (Arnot. at al., supra). and the VK247 (Pv247) or variant type (ANGAGNQPG) (SEQ ID NO: 12) (Rosenberg. R.. et al.. *Circumsporozoite protein heterogeneity in the human malaria parasite Plasmodium vivax*. Science. 1989. 245(4921): p. 973-6). The prevalence of the Pv210 or Pv247 PvCSP sequences varies from geographic area to geographic area. but essentially all Pv parasites have one or the other of the PvCSP sequences. In Thailand, the majority of sporozoites have the Pv210 sequence. while in Colombia. the majority of sporozoites have the Pv247 sequence. Thus. an effective vaccine targeted at the PvCSP repeat region must include both repeats. Limited polymorphism has been observed in the flanking 170 regions (Mann, V.H.. et al, *Sequence variation in the circumsporozoite protein gene of Plasmodium vivax appears to be regionally biased*. Mol Biochem Parasita 1994. 68(1): p. 45-52). During the last decade immunological responses to the PvCSP have been studied (Arevaio-Herrera. M.. at al., *Mapping and comparison of the B-cell epitopes recognized on the Plasmodium vivax circumsporozoite protein by immune Colombians and immunized Aotus monkeys. Ann Trop Med Parasitoi*, 1998. 92(5): p. 539-51), B-cell epitopes have been found throughout the whole sequence (Id.) and both VK210and VK247 are recognized by sera of immune individuals from different malaria endemic areas (See. e.g.. Machado. R.L. and M.M. Povoa, *Distribution of Plasmodium vivax variants* (VK210. VK247 and Pv-like) *in three endemic areas of the Amazon region of Brazil and their correlation with chloroquine treatment*. Trans R Soc Trop Med Hvg, 2000. 94(4): p. 377-81). The VK210 variant contains the PAGDR (SEQ ID NO: 13) sequence. which is recognized in individuals from malaria endemic areas as well as by a monoclonal antibody that protects Saimiri monkeys from challenge with Pv sporozoites. Multiple T helper epitopes recognized in the context of a number of MHC class II haplotypes have also been mapped. One of these epitopes was broadly recognized in individuals from malaria endemic areas of Colombia carrying different class II haplotypes. More recently. using nona- or deca-peptides containing MHC class I binding motifs. peptides capable of stimulating human CD8+T cells from HLA-A*0201 individuals to produce IFN gamma in vitro were identified.

5) Immunization of Saimiri species with PvCSP recombinant proteins (Collins W E, et al. *Immunization of Saimiri sciureus boliviensis with rec vaccines based on the circumsporozoite protein of Plasmodium vivax*. Am J Trop Med. Hyg. 1989 May; 40(5):455-64), and immunization of *Saimiri* sp. with a PvCSP synthetic peptide vaccine (Collins W E, et al. *Protective immunity induced in squirrel monkeys with a multiple antigen construct against the circumsporozoite protein of Plasmodium vivax*. Am J Trop Med. Hyg. 1997 February; 56(2):200-10) have been reported. In the first study there was essentially no protection against sporozoite challenge. In the second study 11 of 26 monkeys were protected against sporozoite challenge, but there was no control group, and there have not been any follow up studies reported. Immunological characterization of the PvCSP has been conducted, and the vaccine potential of 3 long synthetic peptides encompassing the N-terminal (peptide N; position 20-96) and the C-terminal regions (peptide C; position 301-372) as well as a third peptide (peptide R) consisting of 3 copies of the Pv210 9 amino acid repeat region synthesized with the universal T cell epitope P30 (Panina-Bordignon, P., et al., *Universally immunogenic T cell epitopes: promiscuous binding to human MHC class II and promiscuous recognition by T cells*. Eur J Immunol, 1989. 19(12): p. 2237-42; Valmori, D., et al., *Use of human universally antigenic tetanus toxin T cell epitopes as carriers for human vaccination*. J. Immunol, 1992. 149(2): p. 717-21 have been assessed individually in primates with. Montanide ISA 720 as adjuvant. While these peptides/adjuvant preparations are safe well tolerated and immunogenic in humans, limitations on manufacturing long synthetic peptides, and on mixing peptides in a single vaccine, make these compositions poor candidates as human vaccines.

DESCRIPTION OF THE FIGURES

FIG. 2. Coomassie stained SDS-PAGE gels showing gene expression of *Pichia* clones of:

a. Protein 1
b. Protein 2
c. Protein 3

Figure 3:
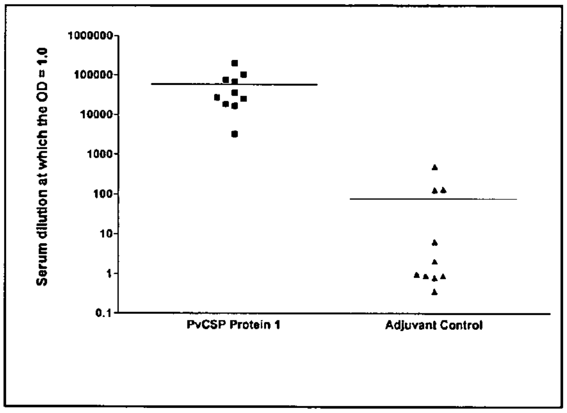

FIG. 3. Antibody to Protein 1 in mice immuniginized with Protein 1

Figure 4:
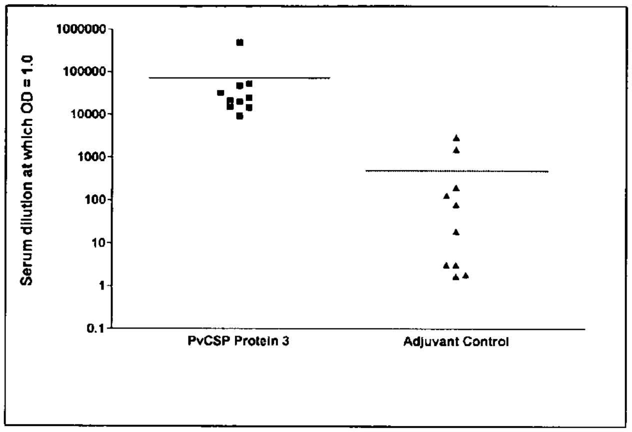

FIG. 4. Antibody to Protein 3 in mice immuniginized with Protein 3

FIG. 5. Antibodies to the PvCSP 210 repeat region peptide (common) in sera of mice immunized with Protein 1 or 3.

FIG. 6. Antibodies to the PvCSP 247 repeat region peptide (variant) in sera of mice immunized with Protein 1 or 3.

Figure 7:
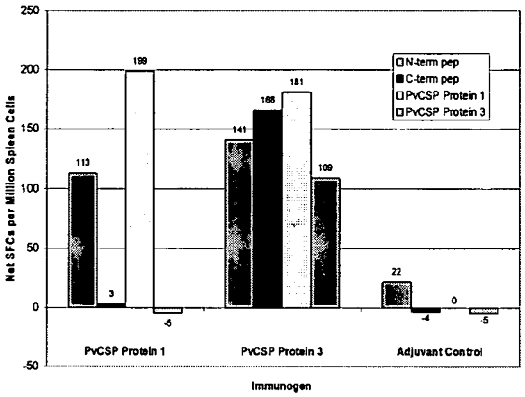

FIG. 7. Interferon gamma ELIspot results in mice immunized with Protein 1 or 3.

SUMMARY

Applicants have created novel polypeptides and novel polynucleotide gene sequences which encode them. The sequences are based upon the known sequence of the circumsporozoite protein of *Plasmodium vivax*. The novel DNA sequencesw per se or as coding sequences in recombinant virus, recombinant bacteria, recombinant parasite, DNA plasmid, or other replicon are useful as production components or compositional components in vaccines, or therapeutics for the prevention and/or treatment of malaria and particularly, malaria caused by *Plasmodium vivax* infection. The polypeptides and, proteins encoded by these gene sequences are similarly useful.

Vaccines directed against *Plasmodium vivax* caused malaria are disclosed which incorporate at least one of these components. Also disclosed are methods of conferring a protective or mitigating immunity against a pathogenic Pv infection and conferring a protective immunity against malaria, symptoms of malaria and Pv caused malaria and malaria symptoms.

Accordingly, it is an object to provide unique proteins and polypeptides incorporating residues in sequence corresponding to portions of the sequences of the repeat regions from the central domain of PvCSP representing both of the naturally occurring common and variant allelic forms of the parasite, the Pv210 and Pv247 PvCSP sequences.

It is an object to provide unique proteins and polypeptides incorporating residues in sequence corresponding to at least 1 copy of each of the Pv210 and Pv247 PvCSP repeat sequences fused to a substantial portion of the amino-terminal region of the PvCSP.

It is an object to provide unique proteins and polypeptides incorporating residues in sequence corresponding to at least 1 copy of each of the Pv210 and Pv247 PvCSP repeat sequences fused to a substantial portion of the carboxy terminal region of the PvCSP.

It is an object to provide unique proteins and polypeptides incorporating residues in sequence corresponding to at least 1 copy of the Pv210 and Pv247 PvCSP repeat sequences fused to substantial portions of both the amino- and the carboxy-terminal regions of the PvCSP.

It is an object to provide unique polynucleotide and DNA sequences, codon optimized sequences and sequences in replicons, wherein the sequences encode segments of the repeat regions from the central domains of both the common and variant forms of PvCSP (representing both of the naturally occurring common and variant allelic forms of the parasite—the Pv210 and Pv247 PvCSP sequences).

It is an object to provide unique polynucleotide and DNA sequences, codon optimized sequences and sequences in replicons, wherein the sequences encode at least one copy of each of both Pv210 and Pv247 PvCSP repeat residues fused to a substantial portion of residues of the amino-terminal region of the PvCSP.

It is an object to provide unique polynucleotide and DNA sequences, codon optimized sequences and sequences in replicons, wherein the sequencers encode at least one copy of Pv210 and Pv247 PvCSP repeat residues fused to a substantial portion of the residues of the carboxy terminal region of the PvCSP.

It is an object to provide unique polynucleotide and DNA sequences, codon optimized sequences and sequences in replicons, wherein the sequencers encode at least one copy of both Pv210 and Pv247 PvCSP repeat residues fused to substantial portions of residues of both the amino and the carboxy terminal regions of PvCSP.

It is an object to provide vaccines comprising the unique proteins polypeptides, polynucleotides and/or DNA sequences disclosed herein.

It is an object to provide methods of conferring a protective or mitigating immunity against malaria, the symptoms of malaria and malaria symptoms caused by pathogenic infection of Pv in subjects, wherein the method comprises administration of unique proteins and/or DNA sequences disclosed herein in vaccine compositions.

DETAILED DESCRIPTION

Three chimeric recombinant and synthetic polypeptides from regions of the circumsporozoite protein of *Plasmodium vivax*, and optimized DNA constructs which encodes them, have been created. Each of these compositions, compositions whose residue sequence is substantially similar to the sequence of any of these compositions, and compositions whose residue sequences correspond to at least about 90% of the sequence of any of these compositions are useful as vaccine components and in immunization regimes to provide protective immunity from malaria and to mitigate the symptoms of malaria upon subsequent challenge with infectious parasites.

Definitions

The terms "about" or "approximately" or "substantially" as used herein mean within an acceptable error range for the particular value as determined by one of ordinary skill in the art, which will depend in part on how the value is measured or determined, i.e. the limitations of the measurement system or the degree of precision required for a particular purpose, e.g. pharmaceutical formulations. For example, "about" can mean within 1 or more than 1 standard deviation as per the practice in the art. Alternatively, "about" can mean a range of up to 20%, preferably up to 10%, more preferably up to 5%, and more preferably up to 1% of a given value. On the other hand the terms can refer to orders of magnitude, preferably within 5-fold, and more preferably with 2-fold of a value. Also, "substantially all" can mean greater than 90%, preferably greater than 95%, or the term can mean a fold increase or fold decrease of 1000 or more, preferably of 5000 or more. Where particular values are used in specification and in the claims, unless otherwise stated, the term "about" means with an acceptable error range for the particular value.

An "immune response" as used herein means a systemic response to the introduction of an immunogen generally characterized by, but not limited to, production of antibody, T cell, or non-specific responses. With regard to a malaria vaccine, the immune response established by a vaccine comprising synthetic, recombinant or naturally occurring *Plasmodium* subunits provides immunity during subsequent challenge by responding to proteins and other immunogens expressed by the sporozoite or other stages of the parasites after they have entered host cells, especially hepatocytes. These immune responses are expected to prevent development of the parasites to the asexual erythrocytic stage that causes disease. An immune response may be a cellular response of increasing production of CD4+ T cells, or CD8+ T cells specific for *Plasmodium* species epitopes, a humoral response of increased production of *Plasmodium*-specific antibodies, or both a cellular and humoral response.

"Mitigate" as defined herein means to substantially reduce, or moderate in intensity, symptoms and pathology of malaria which might manifest subsequent to vaccination.

"Optimized" coding sequences are sequences which have been modified to optimize gene expression. Applicant's extensive experience with expression of proteins in *Pichia pastoris* indicates that altering the codon usage (the degenerative flexibility of the DNA sequence code means multiple triplets code for the same amino acid) based on applicants' proprietary information leads to enhanced expression of the protein (Narum, D L, et al, *Codon Optimization of Gene Fragments Encoding Plasmodium falciparum Merozoites Proteins Enhances DNA Vaccine Protein Expression and Immunogenicity in Mice*. (2001) Infection and Immunity 69:7250-7253). Furthermore, this alteration of codon usage also enhances in vivo expression of proteins in DNA vaccines.

"Parenteral" as defined herein means not through the alimentary canal but rather by introduction through some other route, as subcutaneous, intramuscular, intraorbital, intracapsular, intraspinal, intrasternal, intravenous, transcutaneous etc.

"Prevent" as defined herein means to keep the pathology of malaria from manifesting.

A "replicon" is a genetic unit of replication comprising a length of DNA and a site for initiation of replication. As used herein, a replicon would include a DNA coding sequence operably linked to an initiation sequence or in an expression vector such as a plasmid or a phage.

"Therapeutic" as defined herein relates to reduction of symptoms or pathology which have already become manifest.

A "therapeutically effective amount" as used herein means an amount sufficient to reduce the incidence of disease by at least 30%, preferably 50%, more preferably 75%, and most preferably by at least about 90%.

A "vaccine" as used herein is a composition comprising an antigen and a pharmaceutical carrier. A vaccine may be comprised of a whole infectious agent or components of the infectious agent produced by the infectious agent, another infectious agent or synthetically or recombinantly are administered to stimulate an immune response that will subsequently protect a person from illness caused by that agent. A therapeutic (treatment) vaccine is given after infection and is intended to reduce or arrest disease progression. A preventive (prophylactic) vaccine is intended to prevent initial infection. Agents used in vaccines may be whole-killed (inactive), live-attenuated (weakened), purified components or artificially manufactured components, such as recombinant proteins or synthetic peptides. A vaccine may further comprise a diluent, an adjuvant, a carrier, or combinations thereof, as would be readily understood by those in the art.

"Component" as used herein refers to separate elements of a vaccine regimen, each in turn comprising a discrete vaccine to be administered separately to a subject. Regimens include prime/boost, terminology derived from observation of immune response synergies resulting from combining related DNA and polypeptide component vaccines in a temporal fashion. A vaccine complex comprised of separate components may be referred to as a component vaccine, a component vaccine kit or a component vaccine package, comprising separate vaccine components. For example, a vaccine complex may comprise one or more recombinant or synthetic subunit vaccine components, including but not limited to native polypeptide, recombinant protein, synthetic polypeptide, recombinant virus, recombinant bacteria, recombinant parasite or attenuated or recombinant sporozoites or sporozoite DNA, or RNA. The component vaccines may be administered during a single vaccination session or sequentially over a period of days, weeks or months. Annual booster vaccines are also contemplated.

Protein Constructs—Three novel polypeptides are described below and the sequences are provided:

a) Protein 1 (SEQ ID NO: 1) composed of a segment of the amino region (N-terminus) of PvCSP (75 amino acids) fused to 3 units of the central region repeat (common type, Pv210), fused to 3 units of the central region repeat (variant type, Pv247)=(N+3Rc3Rv).

b) Protein 2 (SEQ ID NO: 3) composed of 3 units of the central region repeat (common type, Pv210), fused to 3 units of the central region repeat (variant type, Pv247), fused to the majority of the carboxyl region (C-terminus) of PvCSP (83 amino acids)=(3Rc3Rv+C)

c) Protein 3 (SEQ ID NO: 5), composed of Protein 1 fused to the carboxyl region of Pv CSP (N+3Rc3Rv+C).

The sequences were derived from SEQ ID Numbers 7-10. This approach is unique in that it covers the N-terminal and C-terminal regions of the protein and the two known major variants of the *P. vivax* CSP. This is the first time that the highly immunogenic N-terminal region of the PvCSP is tested in combination with the repeat region, and the first time to our knowledge that the common and variant repeat regions are combined in the same protein with flanking regions. Given the numbers of T cell epitopes included in the constructs, some of which are conserved, and the presence of both repeat sequences, this immunogen should generate immune responses that recognize virtually all Pv parasites in nature. After careful consideration we decided to include 3 copies of each of the repeat regions as opposed to trying to incorporate the entire repeat regions of both variants, something which would have dramatically increased the size of the proteins. It is well known that PAGDR (SEQ ID NO: 13) (most publications mention only AGDR (SEQ ID NO: 14), but unpublished work of one of the inventors [personal communication SL Hoffman] indicates that PAGDR (SEQ ID NO: 13 ) is the critical minimal B cell epitope), a 5amino acid linear sequence from the common PV210 PvCSP sequence is an epitope recognized by a protective monoclonal antibody called NVS3[61]. It is unlikely that this is the only protective epitope within this sequence. Our constructs each include two copies of PAGDR (SEQ ID NO: 13). In the study by Collins et al. (Collins WE, et al. 407 *Protective immunity induced in squirrel monkeys with a multiple antigen construct against the circumsporozoite protein of Plasmodium vivax*. Am J Trop Med Hyg. 1997 Feb:56(2):200-10), 2 copies of the repeat region, including only one copy of PAGDR (SEQ ID NO: 13)

were included in the synthetic peptide which apparently protected 11 of the 26 monkeys. There is no evidence that any repeat region of any Plasmodium sporozoite circumsporozoite protein has a conformational protective epitope; all appear to be linear epitopes as immunization with short linear synthetic peptides can elicit biologically active and protective antibodies (NANP)n (SEQ ID NO: 15) for PfCSP and (QGPGAP)n (SEQ ID NO: 16) for the *P. yoelii* CSP. Thus, the 27 amino acid residue sequence from the variant repeat of PvCSP likely contains a linear B cell epitope. In fact, the 27 amino acid residue sequence is recognized by a mAb and the polyclonal anti-sera we have raised (see EXAMPLE 3).

These unique proteins are functionally distinct in a number of ways from recombinant immunogens previously tested in Saimiri monkeys (Collins et al., stat.), the long synthetic peptides described above which were tested in Aotus monkeys and humans, and all PvCSP-related proteins that have been developed and tested.

1] Each contains multiple repeat regions from the central domains of both of the naturally occurring allelic forms of the parasite, the Pv210 and Pv247 PvCSP sequences, which represent virtually all PvCSP sequences in nature—not just a single repeat region. Thus, these proteins have the possibility of producing protective anti-repeat region antibodies against the vast majority of PvCSPs in nature. All other Pv-related proteins used in vaccines have included only the Pv210 sequence.

2] A subset of the proteins disclosed herein includes both the amino and carboxy terminal regions of the PvCSP as well as central domain repeat elements described above. No other PvCSP recombinant proteins or synthetic peptides have included all these regions and their epitopes. Thus, the chances of eliciting protective immune responses are increased over all other vaccines ever assessed.

3] Two subsets of the proteins disclosed herein include either the N-terminus fused to 3 copies of the Pv210 and Pv247 repeats or the C-terminus fused to 3 copies of Pv210 and Pv247 repeats. No other PvCSP recombinant protein has included all of these domains which include known B and T cell epitopes.

Methods of DNA synthesis are also well known in the art. See, e.g. Uhlmann E. (1988) Gene. Nov. 15; 71(1):29-40. Applicant's experience with expression of proteins in *Pichia pastoris* indicates that altering the codon usage (the degenerative flexibility of the DNA sequence code means multiple triplets code for the same amino acid) leads to enhanced expression of the protein (Narum, D L, et al, Codon Optimization of Gene Fragments Encoding *Plasmodium falciparum* Merozoite Proteins Enhances DNA Vaccine Protein Expression and Immunogenicity in Mice. (2001) Infection and Immunity 69:7250-7253, incorporated in its entirety herein by reference). Furthermore, this alteration of codon usage also enhances in vivo expression of proteins in DNA vaccines. We therefore used native Pv CSP encoding sequences as the basis for creating synthetic genes in which the sequence has been altered to optimize codon usage.

Methods for expressing encoded polypeptides in a DNA plasmid, recombinant virus, recombinant bacteria, replicon, or other DNA or RNA based vaccine delivery system, or to produce a recombinant protein or synthetic peptide are well known in the art.

As a vaccine, the PvCSP recombinant proteins and synthetic peptide are preferably delivered with adjuvant. Any adjuvant may be used. The most commonly used human adjuvants include mineral salts (e.g., aluminum hydroxide and aluminum or calcium phosphate gels). Another class which includes adjuvants approved for human use is oil emulsions and surfactant based formulations (e.g. MF 59, QS 21, AS 02, and Montanide ISA-51 and ISA-720). Other classes include particulate adjuvants (e.g., virosomes, AS 04, and ISCOMS; microbial derivitives (natural and synthetic) (e.g., monophoshoryl lipid A, Detox, AGP, DC Chol, OM-174, CpG motifs, modified LT and CT; endogenous human immunomodulators (e.g., hGM-CSF and hIL-12, Immudaptin; and finally inert vehicles such as gold particles.

Disclosed herein are vaccines and vaccine components which provide partial, enhanced, or full protection of human subjects who have not previously been exposed to a malaria-causing pathogen, or have been exposed, but are not fully protected. The materials and methods disclosed may also be used to reduce the chance of developing a *Plasmodium vivax* infection, reduce the chance of becoming ill when one is infected, reduce the severity of the illness, such as fever, when one becomes infected, reduce the concentration of parasites in the infected person, or to reduce mortality or morbidity from malaria when one is exposed to malaria parasites. In many cases even partial protection is beneficial. For example, a vaccine treatment strategy that results in any of these benefits of about 30% of a population may have a significant impact on the health of a community and of the individuals residing in the community.

Also disclosed are methods for prevention and treatment of malaria in a subject, which methods comprise administering to the subject an amount effective to treat or prevent malaria of a vaccine comprising the novel compositions disclosed herein. The subject to which the vaccine is administered in accordance with these methods may be any human or non-human animal susceptible to infection with the malaria parasite. For such methods, administration can be oral, parenteral, intranasal, intramuscular, or any one or more of a variety of well-known administration routes other than intravenous. Moreover, the administration may be by continuous infusion or by single or multiple boluses.

The effectiveness of treatment of malaria may be readily ascertained by the skilled practitioner by evaluation of infection in red blood cells (erythrocytes) or clinical manifestations associated with malarial infection, for example fatigue, headache, elevated temperature, and coma. Thus a subject with a *P. vivax* infection and symptoms of malaria shows improved or absent clinical manifestations of malaria infection following administration of the novel compositions disclosed herein.

The prevention of Pv malaria by methods disclosed herein is measured by the percent reduction of Pv blood-stage infection and/or clinical manifestations of disease in subjects upon subsequent challenge with or exposure to infectious Pv parasites.

Generating an immune response in a subject can be measured by standard tests of humoral and cellular immunity including, but not limited to, the following: direct measurement of peripheral blood lymphocytes by means known to the art; natural killer cell cytotoxicity assays (Provinciali et al (1992) J. Immunol. Meth. 155: 19-24), cell proliferation assays (Vollenweider et al. (1992) J. Immunol. Meth. 149: 133-135), immunoassays of immune cells and subsets (Loeffler et al. (1992) Cytom. 13: 169-174; Rivoltini et al. (1992) Can. Immunol. Immunother. 34: 241-251); interferon gamma ELIspot assays, and skin tests for cell mediated immunity (Chang et al. (1993) Cancer Res. 53: 1043-1050). For an excellent text on methods and analyses for measuring the strength of the immune system, see, for example, Coligan et al. (Ed.) (2000) Current Protocols in Immunology, Vol. 1, Wiley & Sons.

Therapeutically effective amounts of the compositions are provided as vaccines. The vaccines comprise therapeutically effective amounts of recombinant proteins, synthetic polypeptides, recombinant viruses, recombinant bacteria, recombinant parasites, DNA or RNA encoding recombinant or synthetic polypeptides or combinations of DNA and polypeptides as well as attenuated *Plasmodium* species (particularly including *P. vivax* or *P. falciparum*) sporozoites, as components in a regimen. Methods of administration of peptide, protein, recombinant viruses, bacteria, and parasite, DNA or RNA vaccines are known in the art. As used herein, the term "administration" or "administering" refers to the process of delivering an agent to a subject, wherein the agent directly or indirectly increases the titer of anti-PvCSP immune responses within the subject. The process of administration can be varied, depending on the agent, or agents, and the desired effect. Thus, the process of administration involves administering a selected immunogen to a patient in need of such treatment. Administration can be accomplished by any means appropriate for the therapeutic agent, for example, by parenteral, mucosal, pulmonary, topical, catheter-based, or oral means of delivery. Parenteral delivery can include for example, subcutaneous, intradermal, intravenous, intramuscular, intra-arterial, and injection into the tissue of an organ. Mucosal delivery can include, for example, intranasal delivery, preferably administered into the airways of a patient, i.e., nose, sinus, throat, lung, for example, as nose drops, by nebulization, vaporization, or other methods known in the art. Pulmonary delivery can include inhalation of the agent. Oral delivery can include delivery of a coated pill, or administration of a liquid by mouth. Administration can generally also include delivery with a pharmaceutically acceptable carrier, such as, for example, a buffer, a polypeptide, a peptide, a polysaccharide conjugate, a liposome, and/or a lipid, according to methods known in the art.

Disclosed herein are unique synthetic and recombinant DNA and polypeptide compositions which correspond to various regions of PvCSP. The biological activities of these compositions are useful as vaccine components. It is known that the entire sequence of a polypeptide (and consequently the DNA which encodes it) may not be required in order to provide some or all of the desired biological activity. This is particularly true with regard to immune response in which one or more epitopes of only a few residues (as few as about 5-10) may be responsible for some or all of the immune response. Compositions in which up to about 10% of the residues have substituted will retain some or all of the immunogenicity of the parent composition. Similarly, truncated compositions with sequences corresponding to a portion, preferably 50% or more, of the full sequence of a biologically active polypeptide demonstrates some or all of the biological activity of the full sequence. Compositions in which sequences are either truncated or substituted relative to the parent sequence are referred to as corresponding sequences. Compositions with sequences corresponding to 90% of a full sequence are considered within the scope contemplated herein, and it is envisioned that DNA and polypeptide compositions with sequences that correspond to at least about 90% of the sequences disclosed are equivalent to their parent compositions.

Compositions of the subject invention can be formulated according to known methods for preparing pharmaceutically useful compositions. Formulations are described in a number of sources which are well known and readily available to those skilled in the art. For example, Remington's Pharmaceutical Science (Martin E W [1995] Easton Pa., Mack Publishing Company, 19th ed.) describes formulations which can be used in connection with the subject invention. Formulations suitable for parenteral administration include, for example, aqueous sterile injection solutions, which may contain antioxidants, buffers, bacteriostats, and solutes which render the formulation isotonic with the blood of the intended recipient; and aqueous and nonaqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the formulations of the subject invention can include other agents conventional in the art having regard to the type of formulation in question.

Therapeutically effective and optimal dosage ranges for vaccines and immunogens can be determined using methods known in the art. Guidance as to appropriate dosages to achieve an anti-viral effect is provided from the exemplified assays disclosed herein. More specifically, results from the immunization pattern described herein can be extrapolated by persons having skill in the requisite art to provide a test vaccination schedule. Volunteer subjects or test animals can be inoculated with varying dosages at scheduled intervals and test blood samples can be evaluated for levels of antibody and/or sporozoite neutralizing activity present in the blood, using the guidance set forth herein for evaluation of rabbit blood. Such results can be used to refine an optimized immunization dosage and schedule for effective immunization of mammalian, specifically human, subjects.

Methods of formulating pharmaceutical compositions and vaccines are well-known to those of ordinary skill in the art (see, e.g., Remington's Pharmaceutical Sciences, $18^{th}$ Edition, Gennaro, ed. (Mack Publishing Company: 1990)). Such vaccines may be for administration by oral, parenteral (intramuscular, intraperitoneal, or subcutaneous injection), transdermal (either passively or using iontophoresis or electroporation), transmucosal (nasal, vaginal, rectal, or sublingual) routes of administration or using bioerodible inserts and can be formulated in dosage forms appropriate for each route of administration. In general, vaccines herein comprise recombinant or synthetic components of *Plasmodium* sporozoites, together with pharmaceutically acceptable carriers. Such compositions include diluents of various buffer content (e.g., Tris-HCl, acetate, phosphate), pH and ionic strength; antioxidants (e.g., ascorbic acid, sodium metabisulfite), and preservatives (e.g., Thimersol, benzyl alcohol); incorporation of the material into particulate preparations of polymeric compounds such as polylactic acid, polyglycolic acid, etc. or into liposomes. See, e.g., Remington's Pharmaceutical Sciences, 18th Ed. (1990, Mack Publishing Co., Easton, Pa. 18042) pages 1435-1712 which are herein incorporated by reference.

Contemplated for use herein are oral solid dosage forms, which are described generally in Remington's Pharmaceutical Sciences, 18th Ed. 1990 (Mack Publishing Co. Easton Pa. 18042) at Chapter 89, which is herein incorporated by reference. Solid dosage forms include tablets, capsules, pills, troches or lozenges, cachets, pellets, powders, or granules. Also, liposomal or proteinoid encapsulation may be used to formulate the present compositions (as, for example, proteinoid microspheres reported in U.S. Pat. No. 4,925,673). Liposomal encapsulation may be used and the liposomes may be derivatized with various polymers (e.g., U.S. Pat. No. 5,013,556). A description of possible solid dosage forms for the therapeutic is given by Marshall, K. In: Modern Pharmaceutics Edited by G. S. Banker and C. T. Rhodes Chapter 10, 1979, herein incorporated by reference. In general, the formulation will include the therapeutic agent and inert ingredients which allow for protection against the stomach environment, and release of the biologically active material in the intestine.

Vaccines for parenteral administration include sterile aqueous or non-aqueous solutions, suspensions, or emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain adjuvants, preserving, wetting, emulsifying, and dispersing agents. They can also be manufactured using sterile water, or some other sterile injectable medium, immediately before use.

In order to determine the effective amount of the vaccines, the ordinary skilled practitioner, considering the therapeutic context, age, and general health of the recipient, will be able to ascertain proper dosing. The selected dosage depends upon the desired therapeutic effect, on the route of administration, and on the duration of the treatment desired. The dosing schedule may vary, depending on the circulation half-life and the formulation used. Approaches to determine levels for dosages are known in the art. Animal models of malaria are known to those in the art. These include non-human primates, of which one used for *P. vivax* and *P. falciparum* is the Aotus monkey (Jones et al. (2000) Am. J. Trop. Med. Hyg., 62: 675-680).

Vaccines may be administered in conjunction with one or more additional active ingredients, pharmaceutical compositions, or vaccines.

The pharmaceutical composition may be preserved, cryopreserved, lyophilized, refrigerated, or the like. A kit may additionally comprise carrier, either in combination with or separate from the pharmaceutical composition. A kit may additionally comprise means for delivery of the pharmaceutical composition, such as syringe and needle or microneedle, or alternatively, any of the means for delivery provided in the instant specification.

Disclosed vaccines and disclosed methods of using these vaccines may be useful as separate elements of a vaccine regimen, each in turn comprising a discrete vaccine to be administered separately to a subject. Regimens may include prime/boost, preferably combining *Plasmodium*-related DNA vaccine or recombinant virus comprising Adenovirus as a prime and polypeptide vaccine as a boost. A vaccine complex comprising separate components may be referred to as a vaccine regimen, a prime/boost regimen, component vaccine, a component vaccine kit or a component vaccine package, comprising separate vaccine components. For example, a vaccine complex may comprise as a component one or more recombinant or synthetic subunit vaccine components disclosed herein, including but not limited to recombinant protein, synthetic polypeptide, DNA encoding these elements per se or functionally incorporated in recombinant virus, recombinant bacteria, or recombinant parasite. Another vaccine component may comprise one or more of these compositions or *Plasmodium*-related native DNA, native protein, or attenuated or recombinant sporozoites or sporozoite DNA, or RNA—from the same or other *Plasmodium* species.

Both the foregoing description and the following examples are exemplary and explanatory only and are not restrictive of the invention, as claimed. Moreover, the invention is not limited to the particular embodiments described, as such may, of course, vary. Further, the terminology used to describe particular embodiments is not intended to be limiting, since the scope of the present invention will be limited only by its claims.

With respect to ranges of values, the invention encompasses each intervening value between the upper and lower limits of the range to at least a tenth of the lower limit's unit, unless the context clearly indicates otherwise. Further, the invention encompasses any other stated intervening values. Moreover, the invention also encompasses ranges excluding either or both of the upper and lower limits of the range, unless specifically excluded from the stated range.

Unless defined otherwise, the meanings of all technical and scientific terms used herein are those commonly understood by one of ordinary skill in the art to which this invention belongs. One of ordinary skill in the art will also appreciate that any methods and materials similar or equivalent to those described herein can also be used to practice or test the invention. Further, all publications mentioned herein are incorporated by reference.

It must be noted that, as used herein and in the appended claims, the singular forms "a," "or," and "the" include plural referents unless the context clearly dictates otherwise. Thus, for example, reference to "a sporozoite subunit vaccine" includes a plurality of such subunits and reference to "the agent" includes reference to one or more agents and equivalents thereof known to those skilled in the art, and so forth.

All numbers expressing quantities of ingredients, reaction conditions, % purity, and so forth, used in the specification and claims, are modified by the term "about," unless otherwise indicated. Accordingly, the numerical parameters set forth in the specification and claims are approximations that may vary depending upon the desired properties of the present invention. At the very least, and not as an attempt to limit the application of the doctrine of equivalents to the scope of the claims, each numerical parameter should at least be construed in light of the number of reported significant digits, applying ordinary rounding techniques. Nonetheless, the numerical values set forth in the specific examples are reported as precisely as possible. Any numerical value, however, inherently contains certain errors from the standard deviation of its experimental measurement.

Obviously, many modifications and variations of the present invention are possible in light of the above teachings. It is therefore to be understood that, within the scope of the appended claims, the invention many be practiced otherwise than as specifically described.

The following examples further illustrate the invention. They are merely illustrative of the invention and disclose various beneficial properties of certain embodiments of the invention. These examples should not be construed as limiting the invention.

EXAMPLES

Example 1

Expression and Purification of Proteins 1-3

1) Expression in the *P. pastoris* Yeast Expression System

Figure 1:
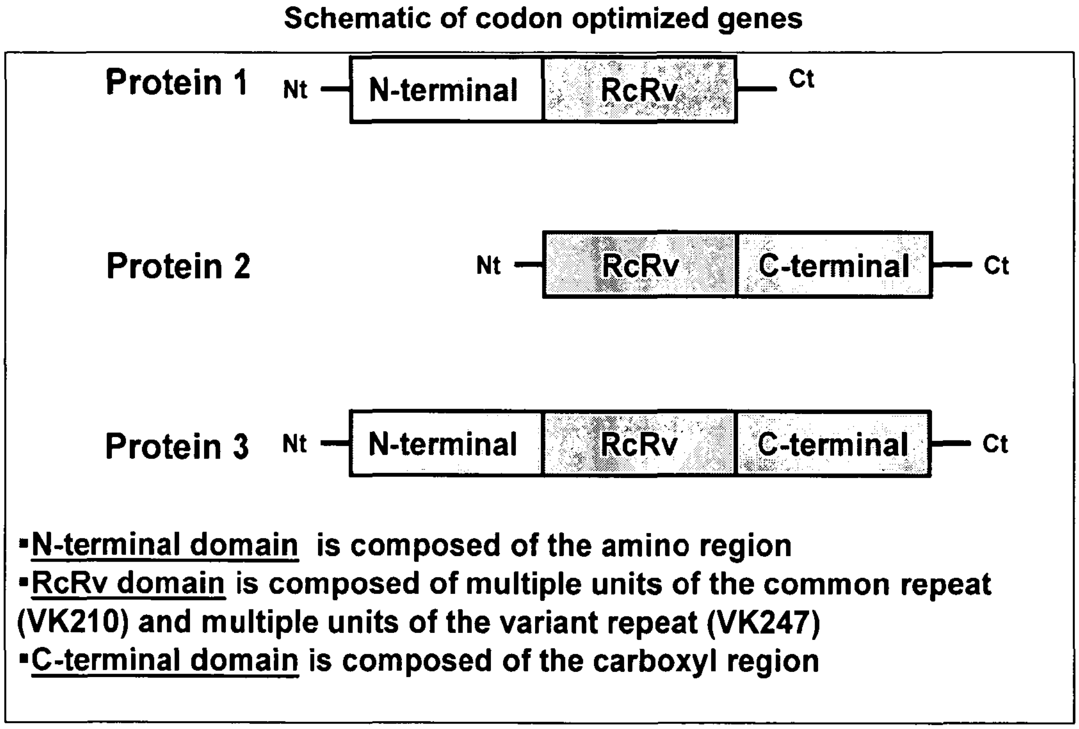
FIG. 1. Schematic illustration of codon optimized genes.

A. Codon Optimization and Gene Synthesis. There are considerable differences in the codon usage between *Plasmodium vivax* and *P. pastoris*. We modified DNA sequences of the gene encoding PvCSP, while maintaining the integrity and identity of the encoded recombinant or synthetic PvCSP. We targeted for modification, stretches of AT sequences and optimized for codon usage, in *P. pastoris*. The synthetic gene was synthesized by Retrogen Inc. Codon optimization significantly enhanced expression. A schematic of the gene products that were targeted for expression is shown in FIG. 1.

B. Gene cloning into *P. pastoris*. The genes encoding Proteins 1, 2 and 3 were amplified separately by PCR using high fidelity DNA polymerase PfuI with primers containing linkers with XhoI and XbaI restriction sites. The amplified gene products encoding Proteins 1, 2 or 3 were of the expected sizes of ~400, ~410 and ~650 bp respectively when analyzed on an eithidium bromide stained 0.8% agarose gel (data not shown). The PCR products were gel purified, digested with XhoI and XbaI restriction enzymes, ligated into the XhoI/XbaI sites of the plasmid pPICZαA, and transformed into *E. coli* Top10 strain. The clones containing plasmids pPICZαA/PvCSPV1, pPICZαA/PvCSPV2 and pPICZαA/PvCSPV3 were selected. Each of these plasmids was sequence verified to be correct. The plasmids were purified, linearized with PmeI restriction enzyme and transformed into *P. pastoris* host strain X33 (for plasmids encoding Protein 1 and 2) and X33/PDI strain for plasmid encoding Protein 3. The clone transformants were plated each onto 100, 200 and 500 μg/mL YPD+Zeocin plates. For each gene construct, four transformants were picked from each dose plate and streaked for single colony separation. The single clones were designated X33/pPICZαA/PvCSPv1/1/1-12, X33/pPICZαA/PvCSPv2/2/1-12 and PDI/pPICZαA/PvCSPv3/1/1-12. A single colony for each clone was inoculated into BMGY and the P1 glycerol stocks were saved and the rest of culture was used for testing expression. The cloning strategy resulted in expression of target genes that were driven by the alcohol oxidase AOX1 promoter that is inducible with methanol.

C. Gene Expression and Optimization of Expression.

A test expression study selected for clones with the most robust expression for each of the proteins. All clones were picked and screened for their protein expression levels in Western blots using monoclonal antibodies specific against the common repeat (Pv210) and/or the variant repeat (Pv247). The parameters studies were temperature and time of induction. Single colonies derived from those transformants were grown in BMGY/BMMY medium (100 mM Potassium phosphate, pH 5.6, 1% yeast extract, 2% peptone, 1.34% yeast nitrogen base without amino acids, $4\times10^{-5}$% biotin, 1% glycerol for BMGY and 0.5% methanol for BMMY) and induced at both 24° C. and 30° C. to test their productivities. The supernatants from 24, 48 h 72, 96 and 120 hours post induction times were analyzed on both Coomassie stained SDS-PAGE gels and blots.

Figure 2:
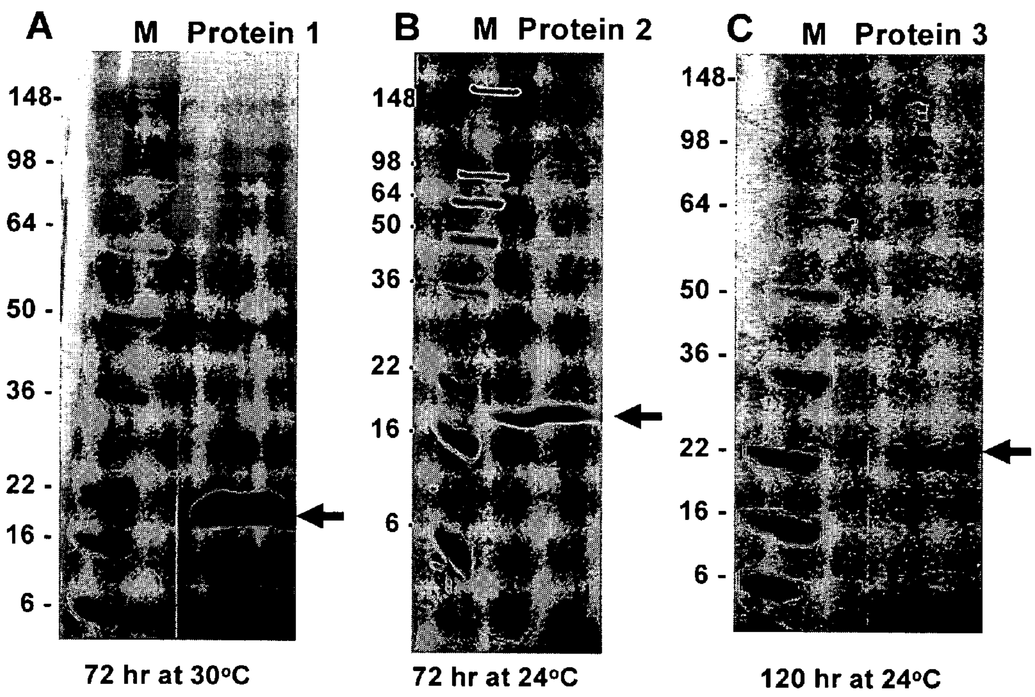

Expression of Protein 1. Expression studies for Protein 1 showed higher productivity in a 120 hour time course and highest expression was observed for Protein 1, clone #4 at 72 hours of induction at 30° C. The estimated expression levels for Protein 1 without any optimization is ~1 g/L (FIG. 2A). Based on the test expression study results, clone #4 (X33/pPICZαA/PvCSPv1/1/4) was chosen as the production clone based on robustness of growth and expression.

Expression of Protein 2. Results from expression studies for Protein 2 selected clone #11 (X33/pPICZαA/PvCSPv2/2/11) with highest productivity in a 120 hour time course study at 48 h induction induced at 24° C. (FIG. 2B). Expression levels were estimated at 150 μg/mL.

Expression of Protein 3. Cloning for Protein 3 included using a GS115 pPIC3.5-PDI *P. pastoris* strain in order to enhance protein expression. Studies identify a clone #12 expressing Protein 3 (PDI/pPICZαA/PvCSPv3/1/12) having higher productivity in a 120 hr time course. The highest expression for clone #12 was at 120 h induction at 24° C. (FIG. 2C). Expression levels were estimated at ~50 Mg/mL.

Example 2

Antigenicity of PvCSP Protein 3 in Human Sera Antibodies

Experiments were conducted to determine if Protein 3 was recognized by antibodies in sera of people naturally exposed to *P. vivax* sporozoites. Sera were obtained from 4 malaria naïve adults from Cali, Colombia (controls) and 190 adults who lived in a *P. vivax* endemic area on the Caribbean coast of Colombia. The sera were assessed at a dilution of 1:100 in an enzyme linked immunosorbent assay (ELISA) in which 125 ng of PvCSP Protein 3 were used per well. Among the 4 controls the optical densities (450 nm) at a serum dilution of 1:100 were 0.081, 0.131, 0.233 and 0.184. The mean optical density of the controls plus three standard deviations was 0.354. Sera from the individuals from the *P. vivax* endemic area were assessed at a serum dilution of 1:100 and any optical density greater than 0.354 was considered positive since there would be a 99% chance that this would be greater than the control sera. The optical densities of the sera from the endemic area ranged from 0.042 to 1.9. Of the 190 sera, 117 (61.6%) had optical densities greater than 0.354 indicating that they contained antibodies to the *P. vivax* circumsporozoite protein, and that the protein was antigenic. Thirty of the sera had optical densities greater than 1.0. The mean optical density of the 117 positive sera was 0.813. This demonstrates that PvCSP Protein 3 is antigenic.

Example 3

Immunogenicity of PvCSP proteins 1 & 3 in Mice Antibodies

Having established that Protein 3 was antigenic (recognized by antibodies in human sera) groups of 10 BALB/c mice were immunized with either PvCSP Protein 1 (N-terminus+3×210 and 3×247 repeats) or PvCSP Protein 3 (N-terminus+3×210 and 3×247 repeats+C-terminus). The proteins were emulsified in Montanide ISA 720 adjuvant (Seppic Inc). A control group of 10 mice received adjuvant alone. Mice received 30 ug of protein subcutaneously 3 times at 2 week intervals. Fourteen days after the third dose, the mice were bled to obtain sera. The sera were tested by ELISA for antibodies: a) to recombinant PvCSP; b) to synthetic peptides containing either the 210 or 247 repeats of native protein; c) to *P. vivax* sporozoites by the indirect fluorescent antibody test (IFAT) using *P. vivax* sporozoites that had either the 210 or 247 repeats; and d) that had biologic activity against live *P. vivax* sporozoites by the inhibition of liver stage development assay (ILSDA).

A. Antibodies to the proteins. Mice immunized with PvCSP Protein 1 developed antibody responses to PvCSP Protein 1 (FIG. 3), and mice immunized with PvCSP Protein 3 developed antibody responses to PvCSP Protein 3 (FIG. 4). These data indicated that proteins were immunogenic.

B. Antibodies to synthetic peptides that included only repeat region amino acid sequences. Mice immunized with PvCSP Protein 1 or with PvCSP Protein 3 developed antibody responses to the 210 synthetic peptide (FIG. 5), and to the 247 synthetic peptide (ANGAGNQPG) (SEQ ID NO: 12) (FIG. 6). These data indicated that despite creating an artificial protein with 3 copies of each of the repeat sequences in tandem (210and 247), immunization with the protein induced antibodies to both sequences.

C. Antibodies to *P. vivax* sporozoites by the indirect fluorescent antibody test (IFAT). Pooled sera from mice (n=10/group) immunized with PvCSP Protein 1, PvCSP Protein 3, or adjuvant alone were assessed for antibodies to native protein on *P. vivax* sporozoites by IFAT. Monoclonal antibody made against the repeat region of PvCSP, NVS3 was used as a positive control. The data in Table 1 demonstrate that mice immunized with PvCSP Protein 1 or PvCSP Protein 3 developed antibody responses to 210 *P. vivax* sporozoites. The same anti-sera were then screened against 247 *P. vivax* sporozoites. The pooled control serum was negative at a dilution of 1:50 and sera from mice immunized with PvCSP Protein 1 or PvCSP Protein 3 were positive at serum dilutions of 1:50 and 1:500, but have not yet been titered. These data demonstrated that mice immunized with PvCSP Protein 1 or PvCSP Protein 3 had antibodies that recognized 210 and 247 PvCSP on whole sporozoites.

Table 1 shows monoclonal antibody NVS3 (initial concentration 500 ug/ml), and sera from mice immunized with 3 doses of PvCSP Protein 1, PvCSP Protein 3, or adjuvant alone (Control), assessed by IFAT against *P. vivax* sporozoites. Sera were considered positive if fluorescence was ≧2+. The control serum was negative at a serum dilution of 1:50. The NVS3 mAb was positive at 78 ng/mL. The anti-sera from Protein 1 and Protein 3 immunized mice were positive at serum dilutions of 1:3200 and 1:6400 respectively.

TABLE 1

| | SERUM DILUTION | | | | | | | | | |
|---|---|---|---|---|---|---|---|---|---|---|
| | Antiserum | | | | | | | | | |
| | 50 | 100 | 200 | 400 | 800 | 1600 | 3200 | 6400 | 12800 | 25600 |
| Control | 1+ | 1+ | 1+ | −ve | −ve | −ve | −ve | −ve | −ve | −ve |
| NVS3 | 3+ | 3+ | 3+ | 3+ | 3+ | 3+ | 2+ | 2+ | 1+ | −ve |
| Protein 1 | 3+ | 3+ | 3+ | 3+ | 3+ | 3+ | 2+ | 1+ | 1+ | −ve |
| Protein 3 | 3+ | 3+ | 3+ | 3+ | 3+ | 3+ | 3+ | 2+ | 1+ | 1+ |

Inhibition of Liver Stage Development Assay (ILSDA) using *P. vivax* (India VII, 210) Sporozoites. Pooled sera from mice immunized with adjuvant alone (Control), PvCSP Protein 1, or PvCSP Protein 3 were assessed for biologically active antibodies by assessing their capacity to inhibit invasion and development of *P. vivax* sporozoites in a human hepatoma cell line, which supports invasion and development of *P. vivax* sporozoites (Table 2). NVS3 mAb at a concentration of 100 µg/mL was used as the positive control. When injected into monkeys prior to intravenous challenge of the monkeys with *P. vivax* sporozoites, this mAb protected the monkeys against infection (Charoenvit, Y., et al., *Inability of malaria vaccine to induce antibodies to a protective epitope within its sequence*. Science, 1991. 251(4994): p. 668-71). The data demonstrate that the NVS3 mAb (94%) and the sera from mice immunized with PvCSP Protein 1 (81%) and PvCSP Protein 3 (83%) inhibited *P. vivax* sporozoite invasion and development in human hepatoma cells.

In Table 2, the effect of anti-sera and NVS3 mAb on invasion and development of *P. vivax* sporozoites in human hepatoma cells is shown. Sporozoites were incubated with medium alone, antibody or antiserum for 3 h then in medium alone until 72 h. The percent invasion inhibition is calculated relative to control serum.

TABLE 2

| Test material | Mean number of parasites per well (±SD) (n = 3) | Percent Invasion Inhibition |
|---|---|---|
| Medium (control) | 527.67 ± 28.71 | NA |
| Control mouse serum (adjuvant only) | 470.00 ± 36.35 | NA |
| NVS3 mAb to PvCSP (100 µg/mL) | 26.67 ± 6.03 | 94% |
| Anti-PvCSP Protein 1 mouse serum (1:20) | 89.33 ± 13.50 | 81% |
| Anti-PvCSP Protein 3 mouse serum (1:20) | 80.33 ± 13.01 | 83% |

This shows that mice immunized with PvCSP Protein 1 or PvCSP Protein 3 have antibodies to the proteins, both PvCSP repeat regions (210 and 247), and to native protein on sporozoites with PvCSP 210 and sporozoites with PvCSP 247. Most importantly the antibodies induced by immunization with PvCSP Protein 1 and PvCSP Protein 3 have significant biological activity. At a serum dilution of 1:20 they inhibit sporozoite invasion and development in human hepatoma cells by 81% and 83%, which is not dissimilar to the 94% inhibitory activity of the protective monoclonal antibody, NVS3, at a concentration of 100 µg/mL.

Example 4

Immunogenicity of Proteins in Mice-T Cells

To characterize T cell responses, Interferon Gamma (IFN gamma) ELIspot assays were conducted. Seventeen days after the third dose of vaccine, a fourth dose was administered. Nine days after this fourth dose the mice were euthanized, their spleens were removed, the splenocytes were isolated and IFNgamma ELIspot assays were set up. The spleen cells were incubated for 36 hours with medium alone or with one of four different antigens: 1) N-terminal peptide (amino acid residues 20-96 of the PvCSP); 2) C-terminal peptide (amino acid residues 301-372 of the PvCSP); 3) PvCSP Protein 1 (N-terminus+210 and 247 repeats); and 4) PvCSP Protein 3 (N-terminus+210 and 247 repeats+C-terminus). After 36 h the wells were assessed for IFN gamma spot forming cells (SFCs). The number of SFCs found in wells with medium alone were considered background and were subtracted from the total SFCs found in wells with the antigens to provide the Net SFCs. These numbers were then adjusted to reflect the numbers of SFCs per million splenocytes. For example if 400,000 cells were placed per well and there was a mean of 100 interferon gamma SFCs in this well with 400,000 splenocytes, the number 100 would be multiplied by 2.5 (=250) to give the number of SFCs per million splenocytes. The results (FIG. 7) demonstrate that: 1) Immunization controls (adjuvant alone) showed no significant response to any antigen; 2) The PvCSP Protein 1-immunized mice (N-terminus+both repeats) responded to the N-terminus peptide (as expected), did not respond to the C-terminus peptide (as expected), responded to PvCSP Protein 1 (as expected), but did not respond to PvCSP Protein 3 (not expected and unexplained). 3) The PvCSP Protein 3 immunized mice (N-terminus+both repeats+C-terminus) responded to all antigens. This shows that mice immunized with PvCSP Protein 1 and with PvCSP Protein 3 had good T cell responses against the PvCSP. As expected, mice immunized with PvCSP Protein 1 only responded to the N-terminus, while mice immunized with PvCSP Protein 3 responded to the both the N- and C-termini.

In the foregoing, the present invention has been described with reference to suitable embodiments, but these embodiments are only for purposes of understanding the invention and various alterations or modifications are possible.

The invention claimed is:

1. An isolated DNA molecule comprising a nucleotide sequence selected from the group consisting of SEQ ID NO: 2, SEQ ID NO: 4 and SEQ ID NO: 6.

2. The isolated DNA molecule of claim 1 wherein the sequence is SEQ ID NO: 2.

3. The isolated DNA molecule of claim 2 operatively linked in a replicon.

4. The isolated DNA molecule of claim 1 wherein the sequence is SEQ ID NO: 4.

5. The isolated DNA molecule of claim 4 operatively linked in a replicon.

6. The isolated DNA molecule of claim 1 wherein the sequence is SEQ ID NO: 6.

7. The isolated DNA molecule of claim 6 operatively linked in a replicon.

* * * * *

```
                          SEQUENCE LISTING


<160> NUMBER OF SEQ ID NOS: 16

<210> SEQ ID NO 1
<211> LENGTH: 129
<212> TYPE: PRT
<213> ORGANISM: Artificial Sequence
<220> FEATURE:
<223> OTHER INFORMATION: Description of Artificial Sequence: Synthetic
      protein construct

<400> SEQUENCE: 1

His Cys Gly His Asn Val Asp Leu Ser Lys Ala Ile Asn Leu Asn Gly
  1               5                  10                  15

Val Asn Phe Asn Asn Val Asp Ala Ser Ser Leu Gly Ala Ala His Val
             20                  25                  30

Gly Gln Ser Ala Ser Arg Gly Arg Gly Leu Gly Glu Asn Pro Asp Asp
         35                  40                  45

Glu Glu Gly Asp Ala Lys Lys Lys Lys Asp Gly Lys Lys Ala Glu Pro
     50                  55                  60

Lys Asn Pro Arg Glu Asn Lys Leu Lys Gln Pro Gly Asp Arg Ala Asp
 65                  70                  75                  80

Gly Gln Pro Ala Gly Asp Arg Ala Asp Gly Gln Pro Ala Gly Asp Arg
                 85                  90                  95

Ala Asp Gly Gln Pro Ala Ala Asn Gly Ala Gly Asn Gln Pro Gly Ala
            100                 105                 110

Asn Gly Ala Gly Asn Gln Pro Gly Ala Asn Gly Ala Gly Asn Gln Pro
        115                 120                 125

Gly


<210> SEQ ID NO 2
<211> LENGTH: 387
<212> TYPE: DNA
<213> ORGANISM: Artificial Sequence
<220> FEATURE:
<223> OTHER INFORMATION: Description of Artificial Sequence: Synthetic
      DNA construct

<400> SEQUENCE: 2

cactgcggcc acaacgtgga cctgtccaag gccatcaacc tgaacggcgt gaacttcaac      60

aacgtggacg cctcctccct gggcgccgcc cacgtgggcc agtccgcctc ccgcggccgc     120

ggcctgggcg agaaccccga cgacgaggag ggcgacgcca agaagaagaa ggacggcaag     180

aaggccgagc ccaagaaccc ccgcgagaac aagctgaagc agcccggaga tagagctgac     240

ggacagcctg ctggagatcg ggccgatgga caacctgccg gagacagagc cgacggccag     300

cccgctgcca acggagccgg aaatcaaccc ggagctaacg gcgctggaaa ccaacctggc     360
```

-continued gctaatggag ctggcaacca gcctgga 387

<210> SEQ ID NO 3
<211> LENGTH: 137
<212> TYPE: PRT
<213> ORGANISM: Artificial Sequence
<220> FEATURE:
<223> OTHER INFORMATION: Description of Artificial Sequence: Synthetic
protein construct

<400> SEQUENCE: 3

Gly Asp Arg Ala Asp Gly Gln Pro Ala Gly Asp Arg Ala Asp Gly Gln
1 5 10 15

Pro Ala Gly Asp Arg Ala Asp Gly Gln Pro Ala Ala Asn Gly Ala Gly
20 25 30

Asn Gln Pro Gly Ala Asn Gly Ala Gly Asn Gln Pro Gly Ala Asn Gly
35 40 45

Ala Gly Asn Gln Pro Gly Pro Asn Glu Lys Ser Val Lys Glu Tyr Leu
50 55 60

Asp Lys Val Arg Ala Thr Val Gly Thr Glu Trp Thr Pro Cys Ser Val
65 70 75 80

Thr Cys Gly Val Gly Val Arg Val Arg Arg Arg Val Asn Ala Ala Asn
85 90 95

Lys Lys Pro Glu Asp Leu Thr Leu Asn Asp Leu Glu Thr Asp Val Cys
100 105 110

Thr Met Asp Lys Cys Ala Gly Ile Phe Asn Val Val Ser Asn Ser Leu
115 120 125

Gly Leu Val Ile Leu Leu Val Leu Ala
130 135

<210> SEQ ID NO 4
<211> LENGTH: 414
<212> TYPE: DNA
<213> ORGANISM: Artificial Sequence
<220> FEATURE:
<223> OTHER INFORMATION: Description of Artificial Sequence: Synthetic
DNA construct

<400> SEQUENCE: 4
ggagatagag ctgacggaca gcctgctgga gatcgggccg atggacaacc tgccggagac 60
agagccgacg gccagcccgc tgccaacgga gccggaaatc aacccggagc taacggcgct 120
ggaaaccaac ctggcgctaa tggagctggc aaccagcctg gacccaacga gaagtccgtg 180
aaggagtacc tggacaaggt gcgcgccacc gtgggcaccg agtggacccc ctgctccgtg 240
acctgcggcg tgggcgtgcg cgtgcgccgc cgcgtgaacg ccgccaacaa gaagcccgag 300
gacctgaccc tgaacgacct ggagaccgac gtgtgcacca tggacaagtg cgccggcatc 360
ttcaacgtgg tgtccaactc cctgggcctg gtgatcctgc tggtgctggc ctaa 414

<210> SEQ ID NO 5
<211> LENGTH: 212
<212> TYPE: PRT
<213> ORGANISM: Artificial Sequence
<220> FEATURE:
<223> OTHER INFORMATION: Description of Artificial Sequence: Synthetic
protein construct

<400> SEQUENCE: 5

His Cys Gly His Asn Val Asp Leu Ser Lys Ala Ile Asn Leu Asn Gly
1 5 10 15

-continued

```
Val Asn Phe Asn Asn Val Asp Ala Ser Ser Leu Gly Ala Ala His Val
            20                  25                  30

Gly Gln Ser Ala Ser Arg Gly Arg Gly Leu Gly Glu Asn Pro Asp Asp
        35                  40                  45

Glu Glu Gly Asp Ala Lys Lys Lys Lys Asp Gly Lys Lys Ala Glu Pro
    50                  55                  60

Lys Asn Pro Arg Glu Asn Lys Leu Lys Gln Pro Gly Asp Arg Ala Asp
65                  70                  75                  80

Gly Gln Pro Ala Gly Asp Arg Ala Asp Gly Gln Pro Ala Gly Asp Arg
                85                  90                  95

Ala Asp Gly Gln Pro Ala Ala Asn Gly Ala Gly Asn Gln Pro Gly Ala
            100                 105                 110

Asn Gly Ala Gly Asn Gln Pro Gly Ala Asn Gly Ala Gly Asn Gln Pro
        115                 120                 125

Gly Pro Asn Glu Lys Ser Val Lys Glu Tyr Leu Asp Lys Val Arg Ala
    130                 135                 140

Thr Val Gly Thr Glu Trp Thr Pro Cys Ser Val Thr Cys Gly Val Gly
145                 150                 155                 160

Val Arg Val Arg Arg Arg Val Asn Ala Ala Asn Lys Lys Pro Glu Asp
                165                 170                 175

Leu Thr Leu Asn Asp Leu Glu Thr Asp Val Cys Thr Met Asp Lys Cys
            180                 185                 190

Ala Gly Ile Phe Asn Val Val Ser Asn Ser Leu Gly Leu Val Ile Leu
        195                 200                 205

Leu Val Leu Ala
    210
```

<210> SEQ ID NO 6
<211> LENGTH: 639
<212> TYPE: DNA
<213> ORGANISM: Artificial Sequence
<220> FEATURE:
<223> OTHER INFORMATION: Description of Artificial Sequence: Synthetic DNA construct

<400> SEQUENCE: 6

```
cactgcggcc acaacgtgga cctgtccaag gccatcaacc tgaacggcgt gaacttcaac      60

aacgtggacg cctcctccct gggcgccgcc cacgtgggcc agtccgcctc ccgcggccgc     120

ggcctgggcg agaaccccga cgacgaggag ggcgacgcca agaagaagaa ggacggcaag     180

aaggccgagc ccaagaaccc ccgcgagaac aagctgaagc agcccggaga tagagctgac     240

ggacagcctg ctggagatcg ggccgatgga caacctgccg gagacagagc cgacggccag     300

cccgctgcca acggagccgg aaatcaaccc ggagctaacg gcgctggaaa ccaacctggc     360

gctaatggag ctggcaacca gcctggaccc aacgagaagt ccgtgaagga gtacctggac     420

aaggtgcgcg ccaccgtggg caccgagtgg accccctgct ccgtgacctg cggcgtgggc     480

gtgcgcgtgc gccgccgcgt gaacgccgcc aacaagaagc ccgaggacct gaccctgaac     540

gacctggaga ccgacgtgtg caccatggac aagtgcgccg gcatcttcaa cgtggtgtcc     600

aactccctgg gcctggtgat cctgctggtg ctggcctaa                            639
```

<210> SEQ ID NO 7
<211> LENGTH: 1137
<212> TYPE: DNA
<213> ORGANISM: Plasmodium vivax -continued

<400> SEQUENCE: 7

```
atgaagaact tcattctctt ggctgtttct tccatcctgt tggtggactt gttccccacg      60
cactgcgggc acaatgtaga tctgtccaag gccataaatt taaatggagt aaacttcaat     120
aatgtagacg ccagttcact tggcgcggca cacgtaggac aaagtgctag ccgaggcaga     180
ggacttggtg agaacccaga tgacgaggaa ggagatgcta aaaaaaaaaa ggatggaaag     240
aaagcagaac caaaaaatcc acgtgaaaat aagctgaaac aaccaggaga cagagcagat     300
ggacagccag caggagacag agcagatgga cagccagcag gtgatagagc agatggacaa     360
ccagcaggag atagagcagc tggacaacca gcaggagata gagcagatgg acagccagca     420
ggagacagag cagatggaca gccagcagga gacagagcag atggacaacc agcaggagac     480
agagcagatg gacaaccagc aggtgataga gcagctggac aaccagcagg tgatagagca     540
gctggacaac cagcaggaga tagagcagat ggacagccag caggagatag agcagctgga     600
cagccagcag gagatagagc agatggacag ccagcaggag atagagcagc tggacagcca     660
gcaggagata gagcagatgg acagccagca ggagatagag cagctggaca gccagcagga     720
gatagagcag ctggacagcc agcaggagat agagcagctg gacagccagc aggagataga     780
gcagctggac agccagcagg aaatggtgca ggtggacagg cagcaggagg aaacgcagga     840
ggaggacagg gacaaaataa tgaaggtgcg aatgccccaa atgaaaagtc tgtgaaagaa     900
tacctagata aagttagagc taccgttggc accgaatgga ctccatgcag tgtaacctgt     960
ggagtgggtg taagagtcag aagaagagtt aatgcagcta acaaaaaacc agaggatctt    1020
actttgaatg accttgagac tgatgtttgt acaatggata agtgtgctgg catatttaac    1080
gttgtgagta attcattagg gctagtcata ttgttagtcc tagcattatt caattaa       1137
```

<210> SEQ ID NO 8
<211> LENGTH: 378
<212> TYPE: PRT
<213> ORGANISM: Plasmodium vivax

<400> SEQUENCE: 8

```
Met Lys Asn Phe Ile Leu Leu Ala Val Ser Ser Ile Leu Leu Val Asp
  1               5                  10                  15

Leu Phe Pro Thr His Cys Gly His Asn Val Asp Leu Ser Lys Ala Ile
             20                  25                  30

Asn Leu Asn Gly Val Asn Phe Asn Asn Val Asp Ala Ser Ser Leu Gly
         35                  40                  45

Ala Ala His Val Gly Gln Ser Ala Ser Arg Gly Arg Gly Leu Gly Glu
     50                  55                  60

Asn Pro Asp Asp Glu Glu Gly Asp Ala Lys Lys Lys Lys Asp Gly Lys
 65                  70                  75                  80

Lys Ala Glu Pro Lys Asn Pro Arg Glu Asn Lys Leu Lys Gln Pro Gly
                 85                  90                  95

Asp Arg Ala Asp Gly Gln Pro Ala Gly Asp Arg Ala Asp Gly Gln Pro
            100                 105                 110

Ala Gly Asp Arg Ala Asp Gly Gln Pro Ala Gly Asp Arg Ala Ala Gly
        115                 120                 125

Gln Pro Ala Gly Asp Arg Ala Asp Gly Gln Pro Ala Gly Asp Arg Ala
    130                 135                 140

Asp Gly Gln Pro Ala Gly Asp Arg Ala Asp Gly Gln Pro Ala Gly Asp
145                 150                 155                 160

Arg Ala Asp Gly Gln Pro Ala Gly Asp Arg Ala Ala Gly Gln Pro Ala
```

-continued

```
                165                 170                 175

Gly Asp Arg Ala Ala Gly Gln Pro Ala Gly Asp Arg Ala Asp Gly Gln
            180                 185                 190

Pro Ala Gly Asp Arg Ala Ala Gly Gln Pro Ala Gly Asp Arg Ala Asp
        195                 200                 205

Gly Gln Pro Ala Gly Asp Arg Ala Ala Gly Gln Pro Ala Gly Asp Arg
    210                 215                 220

Ala Asp Gly Gln Pro Ala Gly Asp Arg Ala Ala Gly Gln Pro Ala Gly
225                 230                 235                 240

Asp Arg Ala Ala Gly Gln Pro Ala Gly Asp Arg Ala Ala Gly Gln Pro
                245                 250                 255

Ala Gly Asp Arg Ala Ala Gly Gln Pro Ala Gly Asn Gly Ala Gly Gly
            260                 265                 270

Gln Ala Ala Gly Gly Asn Ala Gly Gly Gly Gln Gly Gln Asn Asn Glu
        275                 280                 285

Gly Ala Asn Ala Pro Asn Glu Lys Ser Val Lys Glu Tyr Leu Asp Lys
    290                 295                 300

Val Arg Ala Thr Val Gly Thr Glu Trp Thr Pro Cys Ser Val Thr Cys
305                 310                 315                 320

Gly Val Gly Val Arg Val Arg Arg Arg Val Asn Ala Ala Asn Lys Lys
                325                 330                 335

Pro Glu Asp Leu Thr Leu Asn Asp Leu Glu Thr Asp Val Cys Thr Met
            340                 345                 350

Asp Lys Cys Ala Gly Ile Phe Asn Val Val Ser Asn Ser Leu Gly Leu
        355                 360                 365

Val Ile Leu Leu Val Leu Ala Leu Phe Asn
    370                 375
```

<210> SEQ ID NO 9
<211> LENGTH: 711
<212> TYPE: DNA
<213> ORGANISM: Plasmodium vivax

<400> SEQUENCE: 9

```
aagctgaaac aaccagaaga tggggcaggc aatcaaccag gagcaaatgg agcaggcaat      60

caaccaggag caaatggggc aggcaatcaa ccaggagcaa atggggcagg caatcaacca     120

ggagcaaatg gggctggcaa tcaaccagga gcaaatgggg ctggcaatca accaggagca     180

aatggggctg gcaatcaacc aggagcaaat ggggctggca atcaaccagg agcaaatgga     240

gcaggcaatc aaccaggagc aaatggggca ggcaatcaac caggagcaaa tggggctggc     300

aatcaaccag gagcaaatgg agcaggcaat caaccaggag caaatggggc tggcaatcaa     360

ccaggagcaa atggagcagg caatcaacca ggagcaaatg gggcgggcaa tcaaccagga     420

gcaaatgggg ccggcaatca accaggagca aatggggcag gcaatcaacc aggagcaaat     480

ggggctggca atcaaccagg agcaaatggg gcaggtaatc aaccaggagc aaatggtgca     540

ggtggacagg cagcaggagg aaatgctgca aacaaaaagg caggagacgc aggagcagga     600

cagggacaaa ataatgaagg tgcgaatgcc ccaaatgaaa agtctgtgaa agaataccta     660

gataaagtta gagctaccgt tggcaccgaa tggactccat gcagtgtaac c              711
```

<210> SEQ ID NO 10
<211> LENGTH: 237
<212> TYPE: PRT
<213> ORGANISM: Plasmodium vivax -continued

<400> SEQUENCE: 10

```
Lys Leu Lys Gln Pro Glu Asp Gly Ala Gly Asn Gln Pro Gly Ala Asn
  1               5                  10                  15

Gly Ala Gly Asn Gln Pro Gly Ala Asn Gly Ala Gly Asn Gln Pro Gly
             20                  25                  30

Ala Asn Gly Ala Gly Asn Gln Pro Gly Ala Asn Gly Ala Gly Asn Gln
         35                  40                  45

Pro Gly Ala Asn Gly Ala Gly Asn Gln Pro Gly Ala Asn Gly Ala Gly
     50                  55                  60

Asn Gln Pro Gly Ala Asn Gly Ala Gly Asn Gln Pro Gly Ala Asn Gly
 65                  70                  75                  80

Ala Gly Asn Gln Pro Gly Ala Asn Gly Ala Gly Asn Gln Pro Gly Ala
                 85                  90                  95

Asn Gly Ala Gly Asn Gln Pro Gly Ala Asn Gly Ala Gly Asn Gln Pro
            100                 105                 110

Gly Ala Asn Gly Ala Gly Asn Gln Pro Gly Ala Asn Gly Ala Gly Asn
        115                 120                 125

Gln Pro Gly Ala Asn Gly Ala Gly Asn Gln Pro Gly Ala Asn Gly Ala
    130                 135                 140

Gly Asn Gln Pro Gly Ala Asn Gly Ala Gly Asn Gln Pro Gly Ala Asn
145                 150                 155                 160

Gly Ala Gly Asn Gln Pro Gly Ala Asn Gly Ala Gly Asn Gln Pro Gly
                165                 170                 175

Ala Asn Gly Ala Gly Gly Gln Ala Ala Gly Gly Asn Ala Ala Asn Lys
            180                 185                 190

Lys Ala Gly Asp Ala Gly Ala Gly Gln Gly Gln Asn Asn Glu Gly Ala
        195                 200                 205

Asn Ala Pro Asn Glu Lys Ser Val Lys Glu Tyr Leu Asp Lys Val Arg
    210                 215                 220

Ala Thr Val Gly Thr Glu Trp Thr Pro Cys Ser Val Thr
225                 230                 235
```

<210> SEQ ID NO 11
<211> LENGTH: 9
<212> TYPE: PRT
<213> ORGANISM: Plasmodium vivax

<400> SEQUENCE: 11

```
Gly Asp Arg Ala Asp Gly Gln Pro Ala
  1               5
```

<210> SEQ ID NO 12
<211> LENGTH: 9
<212> TYPE: PRT
<213> ORGANISM: Plasmodium vivax

<400> SEQUENCE: 12

```
Ala Asn Gly Ala Gly Asn Gln Pro Gly
  1               5
```

<210> SEQ ID NO 13
<211> LENGTH: 5
<212> TYPE: PRT
<213> ORGANISM: Plasmodium vivax

<400> SEQUENCE: 13

```
Pro Ala Gly Asp Arg
  1               5
```

-continued

```
<210> SEQ ID NO 14
<211> LENGTH: 4
<212> TYPE: PRT
<213> ORGANISM: Plasmodium vivax

<400> SEQUENCE: 14

Ala Gly Asp Arg
  1


<210> SEQ ID NO 15
<211> LENGTH: 4
<212> TYPE: PRT
<213> ORGANISM: Plasmodium vivax

<400> SEQUENCE: 15

Asn Ala Asn Pro
  1


<210> SEQ ID NO 16
<211> LENGTH: 6
<212> TYPE: PRT
<213> ORGANISM: Plasmodium vivax

<400> SEQUENCE: 16

Gln Gly Pro Gly Ala Pro
  1               5
```